(12) United States Patent
Dalton et al.

(10) Patent No.: US 6,623,735 B1
(45) Date of Patent: Sep. 23, 2003

(54) VACCINE CONTAINING A THIOL PROTEASE

(75) Inventors: John P. Dalton, Dublin City University, Dublin 9 (IE); Stuart J. Andrews, Uxbrige (GB)

(73) Assignee: John P. Dalton, Dublin (IE)

( * ) Notice: Subject to any disclaimer, the term of this patent is extended or adjusted under 35 U.S.C. 154(b) by 0 days.

(21) Appl. No.: 08/424,361

(22) PCT Filed: Oct. 21, 1993

(86) PCT No.: PCT/GB93/02172

§ 371 (c)(1),
(2), (4) Date: May 25, 1995

(87) PCT Pub. No.: WO94/09142

PCT Pub. Date: Apr. 28, 1994

(30) Foreign Application Priority Data

Oct. 21, 1992 (GB) ............................................. 9222156
Apr. 2, 1993 (GB) ............................................. 9307028

(51) Int. Cl.[7] .............................................. A61K 38/48
(52) U.S. Cl. .............................. 424/94.65; 424/94.63; 424/94.1; 424/184.1; 424/185.1; 424/191.1; 424/265.1; 424/266.1; 435/183; 435/212; 435/219
(58) Field of Search ........................... 424/265.1, 266.1, 424/184.1, 185.1, 191.1, 94.1, 94.63, 94.65; 530/350; 435/23, 183, 212, 219

(56) References Cited

FOREIGN PATENT DOCUMENTS

| WO | 8603680 | * | 7/1986 | |
|---|---|---|---|---|
| WO | 9008819 | * | 8/1990 | ............ C12N/9/10 |

OTHER PUBLICATIONS

Dowd et al. Biochemical Society Transactions 20(1) : 86 S.*
Carmona et al. Biochemical Society Transactions 20(1) 85S, 1992.*
Yamasaki et al. Jpn J. Parasitology 38(6) : 373–84, 1989.*
Ishidoh et al. FEBS 223(1) : 69–73, 1987.*
Dalton et al. Molecular and Biochemical Parasitology 35:161–166, 1989.*
Heggernan et al. Biochemical Society Transactions vol. 17, Part 2, Apr. 1989.*
Harlow et al Antibodies A Laboratory Manual, Cold Spring Harbor Laboratory pp. 96–111, 1988.*
Dalton et al. Molecular & Biochemical Parasitology, 35(2) : 11–166, 1989.*

* cited by examiner

Primary Examiner—Patricia A. Duffy
(74) Attorney, Agent, or Firm—Rothwell, Figg, Ernst & Manbeck

(57) ABSTRACT

Thiol proteases having Cathepsin 1 type activity are used in the formulation of vaccines for combating helminth parasites. Preferably the protease is derived from a fluke such as *Fasciola hepatica*.

6 Claims, 8 Drawing Sheets

Figure 1A:
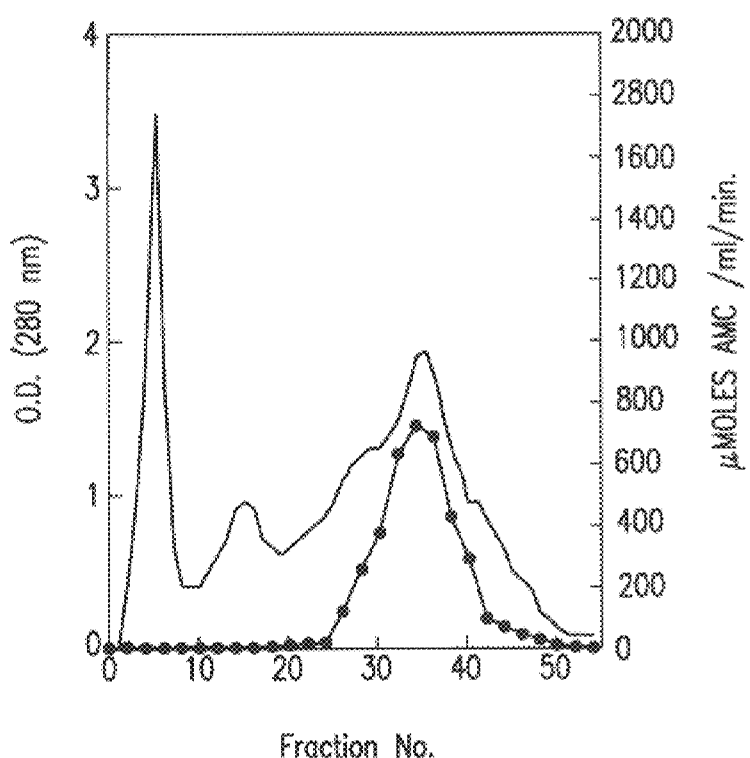

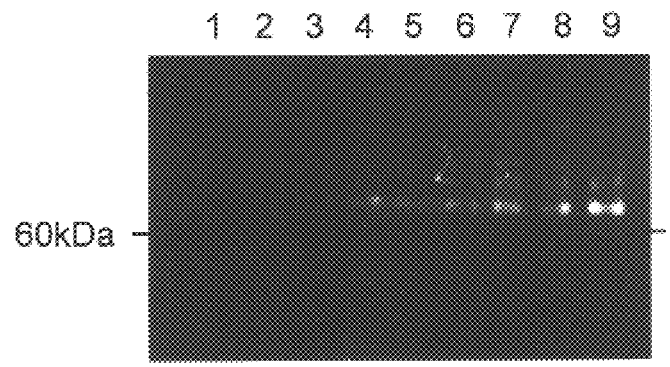
FIG.2A
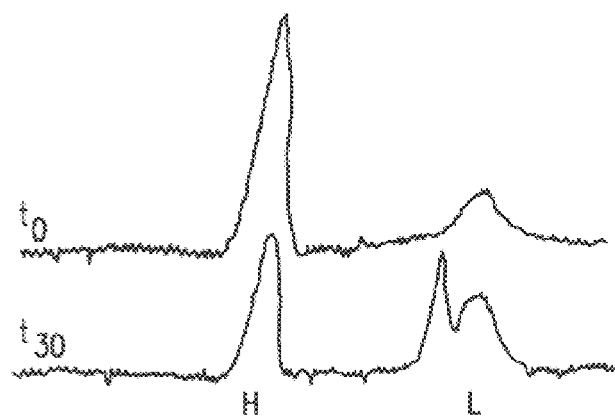
FIG.2B(i)
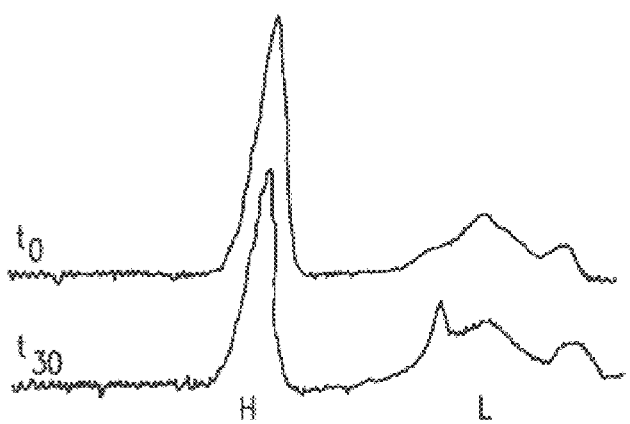
FIG.2B(ii)

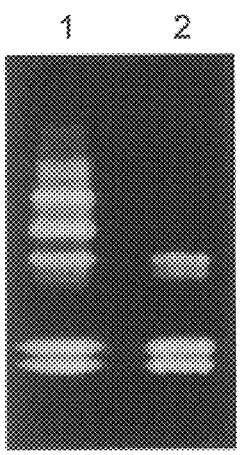 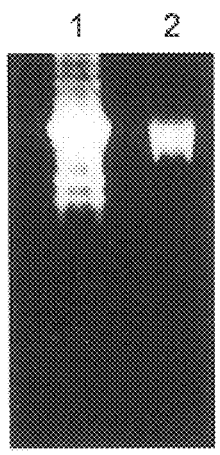 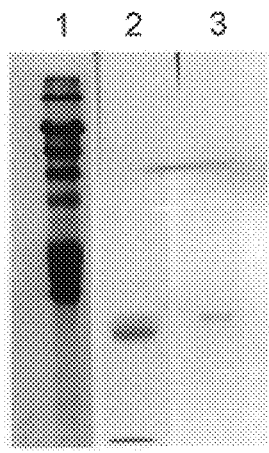
FIG.5A  FIG.5B  FIG.5C
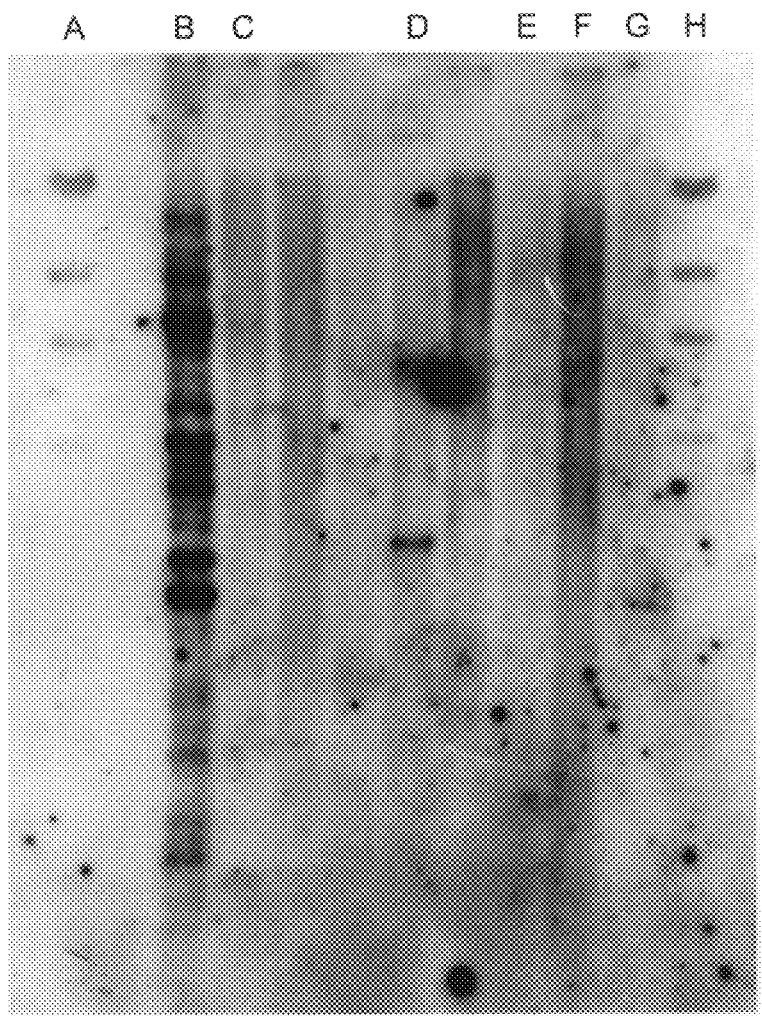
FIG.9

Nucleic Acid Sequence of and Protein coded by JDCLONEC.SEQ

```
                                                                        v
                                                          v             T                                  1
         v                v             v             v             v             v
CAGGGAAACTGTGTNGNNCCTGTTGGGCATTCTCAACAACCGGTACTATGGAGGACAATATATGAAAAACG                                    71
GlnGlyAsnCys?????CysTrpAlaPheSerThrThrGlyTyrMetGluGlyGlnTyrMetLysAsnGlu                                    24 v                v             v             v             v             v
AAAAAACTAGTATTTCATTCTCTGAGCAACAACTGGTCTGATTGTAGCGGTCCTTGGGGAAATAATGGTTG                                   141
LysThrSerIleSerPheSerGlnGlnLeuValAspCysSerGlyProTrpGlyAsnAsnGlyCys                                          47 v                v             v             v             v             v
CAGTGGTGGATTGATGAAAATGCTTACCAATATTTGAAACAATTTGGATTGGAAACCGAATCCTCTTAT                                    211
SerGlyGlyLeuMetGluAsnAlaTyrGlnTyrLeuLysGlnPheGlyLeuGluThrGluSerSerTyr                                       70 v                v             v             v             v             v
CCGTACACGGCTGTGGAAGGTCAGTGTCGATACAATAGGCAGTTGGGAGTTGCCAAAGTGACCGGCTACT                                    281
ProTyrThrAlaValGluGlyGlnCysArgTyrAsnArgGlnLeuGlyValAlaLysValThrGlyTyrTyr                                    94 v                v             v             v             v             v
ATACTGTGCATTCTGGCAGTGAGGTAGAATTGAAAAATCTAGTCGGTTCCGAAGGACCTGCCGCGATCGC                                    351
ThrValHisSerGlySerGluValGluLeuLysAsnLeuValGlySerGluGlyProAlaAlaIleAla                                      117 v                v             v             v             v             v
TGTGGATGTGGAATCTGACTTCATGATGTACAGGAGTGGTATTTATCAGAGCCAAACTTGTTACCGTTC                                    421
ValAspValGluSerAspPheMetMetTyrArgSerGlyIleTyrGlnSerGlnThrCysLeuProPhe                                      140 v                v             v             v             v             v
GCTCTGAATCATGCAGTCTTGTCTGTCGGTTATGAACACAGGATGGTACTGNTT                                                    476
AlaLeuAsnHisAlaValLeuSerValGlyTyrGlnTyrGlyThrGlyAspGlyThr?????                                             158
```

FIG. 6

Nucleic Acid Sequence of and Protein coded by CLONED.SEQ

```
                                                                                v
                                                                                c
                v                      v                      v                 v                                1
CATCAAGAAGCCCNNGGCTCTTGTTGGGNTTTCTCAACAACAGGTGTATGGAAGGACAGTATATGAAAA                                            71
HisGlnGluAla???GlySerCysTrp???PheSerThrThrGlyAlaMetGlyGlnTyrMetLysAsn                                            24
                v                      v                      v                 v                              141
ACCAAAGAACTAGTATTTCATNCTCTGAGCAACAACTGGTCGATTGTAGCCGTGATTTGGCAATTATGG                                           47
GlnArgThrSerIleSer???SerGluGlnGlnLeuValGlnLeuValAspCysSerArgAspPheGlyAsnTyrGly
                v                      v                      v                 v                              211
TTGTAATGGTGGACTAATGGAAAATGCATACGAATATTTGAAACGATTTGGATTGGAAACCGAGTCTTCT                                          70
CysAsnGlyGlyLeuMetGluAsnAlaTyrGluTyrLeuLysArgPheGlyLeuGluThrGluSerSer
                v                      v                      v                 v                              281
TATCCTTACAGGGCTGTGGAAGGACAATGTCGATACAACGAGCAGTTGGGAGTTGCCAAAGTGACTAGCT                                          94
TyrProTyrArgAlaValGluGlyGlnCysArgTyrAsnGluGlnLeuGlyValAlaLysValThrSerTyr
                v                      v                      v                 v                              351
ACTATACGGTACATTCTGGAGATGAGGTAGAATTGCAAAATCTAGTCGGTGCCGAAGGACCTGCTGCGGT                                         117
TyrThrValHisSerGlyAspGluValGluLeuGlnAsnLeuValGlyAlaGluGlyProAlaAlaVal
                v                      v                      v                 v                              421
CGCTTTGGATGTGGAGTCAGACTTCATGATGTACAGGAGTGGTATTATCAGAGCCAAACTTGTTCACCG                                          140
AlaLeuAspValGluSerAspPheMetMetTyrArgSerGlyIleTyrGlnSerGlnThrCysSerPro
                v
GATCGTTTGAACCATGGAGTGTTGNCTGTCGNTTATGGAACNCAGGGTGGTNCTCNC                                                      478
AspArgLeuAsnHisGlyValLeu???Val???TyrGly???Gly???Glny???                                                        158
```

FIG.7

Nucleic Acid Sequence of and Protein coded by CLONEE.SEQ

```
                                                                    N                      1
GCGAAATGTGGTTCCTGTTGGGCATTCTCAACAACCGGTACTATGGAGGGACAATATATGAAAAACGAAA      71
AlaLysCysGlySerCysTrpAlaPheSerThrThrGlyThrMetGlyGlnTyrMetLysAsnGluLys        24

AAACTAGTNTTCANCCTCTGAGCAACAACTGGTCGATTGTAGCGGTCCTTGGGGAAATAATGGTTGCAG      141
ThrSer???Ser???SerGluGlnGlnLeuValAspCysSerGlyProTrpGlyAsnAsnGlyCysSer       47

TGGTGGATTGATGGAAAATGCTTACCAATATTTAAAACAATTTGGAAACCGAATCCTCTTATCCG          211
GlyGlyLeuMetGluAsnAlaTyrGlnTyrLeuLysGlnPheGlyLeuGluThrGluSerSerTyrPro       70

TACACGGCTGTGGAAGGTCAGTGTCGATACAATAGGCCAGTTGGGAGTTGCCAAAGTGACTGGCTACTATA    281
TyrThrAlaValGlyGlyGlnCysArgTyrAsnArgGlnLeuGlyalaLysValThrGlyTyrTyrThr       94

CTGTGCATTCTGGCAGTGAGGCAGGATTGAAAAATCTAGTCGGTTCCGAAGGACCTGCCGCGATCGTGT     351
ValHisSerGlySerGluAlaGlyLeuLysLysAsnLeuValGlySerGluGlyProAlaAlaIleAlaVal   117

GGATGTGGAATCTGACTTCATGATGATACAGGAGTGGTATTTATCAGANCCAAACTTGTTTACCGTTCGCT   421
AspValGluSerAspPheMetMetTyrArgSerGlyIleTyrGln???GlnThrCysLeuProPheAla      140

TTGAATCATGCAGTCTTGNCTGTCGATTATGGAACACAGGATGGTNACNCCC                      473
LeuAsnHisAlaValLeu???ValAspTyrGlyThrGlnAspGly?????????                     157
```

FIG. 8

VACCINE CONTAINING A THIOL PROTEASE

This application claims priority from British Application No. 9222156.3, filed Oct. 21, 1992 and British Application No. 9307028.2, filed Apr. 2, 1993.

FIELD OF THE INVENTION

The invention relates to the use of a class of thiol proteases as protective antigens against helminth parasites, namely the Cathepsin L-like proteases frequently released as excretory/secretory products by such parasites.

DESCRIPTION OF THE RELATED ART

Each species of domestic animal can be parasitised by a number of different species of helminths, a process which usually causes disease. For example the parasitic trematode *Fasciola hepatica* is known to be the cause of the economically important disease fascioliasis in ruminants, such as cattle and sheep. The parasite enters the mammalian host by penetrating the gut wall and spends approximately seven weeks feeding on and burrowing through the liver mass before migrating into the bile duct. Following infection, development of immunity in the host is poor and resistance to reinfection in already infected hosts is only partial or non-existent. Other parasitic flukes include *Fasciola gigantica* and Dicrocoelium spp. and also Paramphistomum spp.

Problems are also caused by nematodes such as hookworms (e.g. Necator, Ancylostoma, Uncinaria and Bunostomum spp.).

Of the blood feeding nematodes the genus Haemonchus infects the lining of the abomasum of ruminants, causing anaemia and weight loss and if untreated frequently leads to death. Animals infected with the related non-blood feeding nematode Ostertagia similarly fail to thrive and may die if untreated.

Other parasitic worms of economic importance include the various species of the following helminth genera: Trichostrongylus, Nematodirus, Dictyocaulus, Cooperia, Ascaris, Dirofilaria, Trichuris and Strongylus. In addition to domestic livestock, pets and humans may also be infected, not infrequently with fatal results and helminth infections and infestations thus pose a problem of considerable worldwide significance.

Control of helminth parasites of grazing livestock currently relies primarily on the use of anthelmintic drugs combined with pasture management. Such techniques are often unsatisfactory firstly, because anthelmintic drugs may have to be administered frequently, secondly because resistance against anthelmintic drugs is becoming increasingly widespread and thirdly because appropriate pasture management is often not possible on some farms and even where it is, it can place constraints on the best use of available grazing.

Numerous attempts have been made to control helminth parasites of domestic animals by immunological means. With very few exceptions (e.g. the cattle lungworm, *Dictyocaulus viviparus*) this has not proved possible.

A vaccine against *F.hepatica* has been proposed in WO90/08819 comprising a glutathione-S-transferase from *F. hepatica* as antigenic material.

Bennett (UK Patent No. 2169606B) extracted various antigens from Fasciola organisms by a process which separates antigens specific to the juvenile stage from antigens present throughout the juvenile and adult stages.

It is known that in vitro cultured *F. hepatica* release protease enzymes which are capable of cleaving immunoglobulins with a papain or Cathepsin-B type of activity (Chapman and Mitchell, Vet. Parasitol. 11 (1982), p. 165–178). It has been suggested that these protease enzymes may assist in evading the immune response in combination with the known ability of the worms to slough off the surface glycocalyx thus shedding bound antibody (Hanna, Exp. Parasitol 50 (1980), p. 155–70). Furthermore crude in vitro excretory/secretory products can under some circumstances confer immunity on rats (Rajasekariah et al, Parasitol. 79 (1979), p. 393–400) perhaps by raising antibodies to such enzymes thus inhibiting them. However, the precise nature of the enzymes is far from clear.

A study of excretory/secretory proteases involving gelatin substrate polyacrylamide gel electrophoresis (GS-PAGE) (Dalton and Heffernan, Mol. Biochem. Parasitol. 35 (1989), p. 161–166) showed a number of cysteine proteases with a wide range of molecular weights and falling generally into two groups, namely from 27.5 KDa to 46 KDa active at pH 4.5"8.0 and from 60 KDa to 88 KDa active at pH 3.0–4.5. It was suggested that the latter group might correspond to the immunoglobulin cleaving enzymes of Chapman and Mitchell and that autolysis and/or aggregation of one or more protease enzymes might be giving the multiple band structure.

Subsequently an HPLC procedure was used and three peaks resolved. Protein from the 15 kDa peak was found to have the ability to cleave IgG at an optimum of pH 4.5 (Heffernan et al, Biochem. Soc. Trans. 19 (1991), page 275).

Another study attempting to characterise the protease enzymes of adult *F. hepatica* is that of Rege et. al. (Mol. Biochem. Parasitol. 35 (1989), p. 89–96) in which a 14,500 Da protein was purified by cation exchange chromatography and molecular sieve HPLC. Maximal hydrolysis of the substrate CBZ-Phe-Arg-AFC was found at pH 6.0. Rege et al used lyophilised whole worms as the source of their protease so that it is not clear whether their protease is excreted or not. They speculated that the protease might be involved in immune evasion or nutrition.

A protease isolated from "Fasciola spp." has been reported by Yamasaki et al. (Japan J. Parasitol., 38 (1989), p. 373–384). The protease had a molecular weight of 27 kDa as determined by sodium dodecyl sulphate polyacrylamide gel electrophoresis (SDS-PAGE), was capable of hydrolysing haemoglobin and this hydrolysing activity was inhibited by cysteine protease inhibitors. Monoclonal antibodies specific for the protease could also inhibit the haemoglbin hydrolysis.

Other studies relating to proteases released by helminth parasites are Fagbemi and Hillyer, Vet. Parasitol. 40 (1991), p. 217–226 relating to *Fasciola gigantica*; Knox and Kennedy, Mol. Biochem. Parasitol. 28 (1988), p. 207–216 relating to Ascaris suum; and Yamakami and Hamajima, Comp. Biochem. Physiol. 87B (1987), p. 643–648 relating to *Paragonimus westermani*.

SUMMARY OF THE INVENTION

It has now been found that the group of cysteine proteases disclosed by Dalton and Heffernan as having a range of molecular weights in the range 27.5–88 KDa on gelatin substrate (GS) PAGE can in fact be resolved as two proteases of 27 KDa and 29.5 by SDS-PAGE under reducing conditions; that these proteases are two distinct Cathepsin L-like activities as determined by substrate specificity, affinity for ion exchange columns and N-terminal sequencing;

that the proteases also have the ability to cleave immunoglobulins; that immunisation of rabbits with purified proteases can stimulate antibodies capable of neutralizing the enzyme activity; and that this discovery opens up the possibility of an effective vaccine against helminth parasites and in particular *F. hepatica* using well-characterised purified protective antigens and avoiding the drawbacks in terms of toxicity and side-effects such as immune suppression or dominance which are inherent in the use of unresolved crude excretory/secretory products.

Accordingly a first aspect of the present invention provides a vaccine for use in combating a parasitic infestation of helminths in a mammal wherein the antigenic material comprises a protease having enzyme activity of the Cathepsin L type, in at least partially purified form, or an antigenic fragment or epitope thereof, together with a carrier and/or adjuvant.

The invention also provides a method of combating a parasitic infestation of helminths in a mammal comprising administering to said mammal a vaccine according to the invention as hereinbefore defined in an amount effective to combat said infestation.

The mammal is preferably a ruminant, for example cattle or sheep, but the vaccine and method of the invention may also find application in humans.

DETAILED DESCRIPTION OF THE INVENTION

Preferably the Cathepsin L-like protease is derived from flukes such as Fasciola or Dicrocoelium, in particular from the liver fluke *Fasciola hepatica*. Alternatively it is preferred that the Cathepsin L-like protease should be capable of stimulating an immune response which will be effective against Fasciola or Dicrocoelium, in particular *F. hepatica* and *F. gigantica*, such Cathepsin L-like-molecules from other species as are capable of conferring a cross-protective immune response thus forming a particularly preferred aspect of the invention.

The *F. hepatica* Cathepsin L-like protease shown hereinafter to possess a molecular weight of approximately 27 KDa by sodium dodecyl sulphate polyacrylamide gel electrophoresis under reducing conditions is particularly preferred for use in the vaccine and method of the invention. This protease also gives an apparent molecular weight by molecular sieve HPLC of 15 KDa. It will be referred to as Cathepsin L1.

The *F. hepatica* Cathepsin L-like protease shown hereinafter to possess a molecular weight of approximately 29.5 kDa by sodium dodecyl sulphate polyacrylamide gel electrophoresis under reducing conditions is also particularly preferred for use in the vaccine and as a novel protein itself forms a further aspect of the invention. This Cathepsin will be referred to as Cathepsin L2 where necessary to distinguish it from Cathepsin L1.

The Cathepsin L-like activity incorporated in the vaccine according to the invention is in at least partially purified form. Preferably the Cathepsin L-like activity comprises at least 75% of the total excretory/secretory proteins present in the vaccine and more preferably the Cathepsin L is at least 95% pure. It will be appreciated that once Cathepsin L of at least 95% purity has been obtained it can be admixed with one or more further purified antigenic proteins, including one or more further excretory/secretory proteins, to form a polyvalent vaccine.

Cathepsin L-like activity can be demonstrated by the ability to cleave the synthetic peptide substrate Z-phe-arg-AMC (benzyloxycarbonyl-L-phenylalanyl-L-arginyl-7-amido-4-methyl coumarin) combined with a relative inability to cleave the related peptides Z-arg-arg-AMC and Z-arg-AMC thus distinguishing the enzyme from Cathepsin B and Cathepsin H. Confirmation of the protease as a Cathepsin L can also be obtained by a comparison of the N-terminal amino acid sequence with the sequences of known Cathepsin L molecules.

Rat liver Cathepsin L, a mammalian Cathepsin L, has been shown to exist as a two chain protein (Ishidoh et al, FEBS Letters 223 (1987), pages 69–73). It is unclear whether or not a similar structure is present in non-mammalian Cathepsin L, although see the amino acid sequencing results presented hereinafter.

The vaccines according to the invention may be formulated with conventional carriers and/or adjuvants and the invention also provides a process for the preparation of the vaccines comprising bringing into association a purified protease having enzyme activity of the Cathepsin L type or an antigenic fragment or epitope thereof and one or more adjuvants or carriers. Suitable adjuvants include aluminium hydroxide, saponin (ISCOMs), muramyl dipeptide, mineral and vegetable oils, DEAE dextran, nonionic block copolymers or liposomes such as Novasomes (Trade Mark of Micro Vesicular Systems Inc.), in the presence of one or more pharmaceutically acceptable carriers or diluents. Carriers for peptide sequences corresponding to epitopes of Cathepsin L-like protease according to the invention can be proteins such as Hepatitis B core antigen multiple antigen peptide or lipopeptides such as tripalmitoyl-S-glycerylcysteinylserylserine ($P_3CSS$). Suitable diluents include liquid media such as saline solution appropriate for use as vehicles. Additional components such as preservatives may be included.

Administration of the vaccine to the host species may be achieved by any of the conventional routes, e.g. orally or parenterally such as by intramuscular injection, optionally at intervals e.g. two injections at a 7–35 day interval. A suitable dose when administered by injection might be such as to give an amount of Cathepsin L-like protein within the range 10–500 μg.

While the Cathepsin L-like protease for use in the vaccine according to the invention may be prepared by isolation from the excretory/secretory products of adult and/or juvenile helminths, it may also be convenient to prepare it by recombinant DNA techniques with the known advantages which such techniques give in terms of purity of product, scaling-up of production and reproducibility. Thus the invention also provides a Cathepsin L-like protease or a proenzyme therefor or an antigenic fragment or epitope thereof, produced by means of recombinant DNA techniques.

Additional aspects of the invention related to the above include DNA molecules encoding for Cathepsin L-like proteases or antigenic fragments or epitopes thereof; vectors containing one or more such DNA sequences; host cells, for example bacteria such as *E. coli* or more preferably eukaryotic cells, transformed by such vectors, for example by a baculovirus vector; and processes for preparing recombinant Cathepsin L-like protease or antigenic fragments or epitopes thereof comprising culturing such transformed host cells and isolating said Cathepsin L-like protease or fragment or epitope from the cultured cells. Since the tertiary structure of the Cathepsin L-like protease is important in the antibody response of a vaccinated animal eukaryotic expression systems are preferred as the tertiary structure will be more faithfully reproduced.

An alternative live or inactivated vaccine formulation may comprise an attenuated or virulent virus or a host cell, e.g. a microorganism such as a bacterium, having inserted therein a DNA molecule according to the invention for stimulation of an immune response directed against polypeptides encoded by the inserted nucleic acid molecule.

Additional antigenic materials may also be present in the vaccine thus giving an enhanced protective effect against the helminth parasite in question or a combined protective effect against one or more additional parasitic infestations.

A yet further aspect of the invention provides a monoclonal or polyclonal antibody capable of inducing immunity to a Cathepsin L-like protease in a mammal when administered to said mammal, the antibody having an affinity for the variable region of one or more further antibodies, said further antibodies having an affinity for said Cathepsin L.

This approach, the so-called "anti-idiotype" approach, permits formulation of a vaccine which will dispense entirely with the original antigen and may offer even greater advantages in terms of safety, avoidance of side effects and convenience of manufacture.

The invention is illustrated by the following examples:

1) CATHEPSIN-L1 PURIFICATION

Mature flukes were obtained from the infected livers of condemned animals at an abattoir. The flukes were washed, cultured overnight, and the culture medium centrifuged as described in Dalton and Heffernan, Mol. Biochem. Parasitol 35 (1989) p. 161–166. 500 ml of the culture medium (E/S) was concentrated to 10 ml by ultrafiltration with a membrane having a 3000 mw cut off and the sample was applied at 4° C. to a 120 ml Sephacryl S-200 column (1.9×42 cm, Pharmacia, Uppsala, Sweden) equilibrated in phosphate buffered saline (PBS) pH 7.3; the void volume of the column was found to be 110 ml. Fractions (volume 5 ml) were collected (after the void volume had been eluted), and they were monitored for protein content at O.D. 280 nm, using a LKB Uvicord monitor. The Cathepsin L-like enzyme activity in the different fractions was assayed using the synthetic fluorogenic peptide Z-Phe-Arg-AMC, known to be specific for Cathepsin-L enzymes. The release of the fluorescent leaving group, 7-amino-4-methylcoumarin (AMC) was monitored in a Perkin-Elmer Luminescence Spectrometer model LS 50, at excitation and emission wavelengths of 370 and 440 nm, respectively (FIG. 1A). Fractions with Cathepsin L-like activity were pooled and applied to a 50 ml QAE Sephadex (Pharmacia, Uppsala, Sweden) column. The column was prepared as follows:

QAE Sephadex A-50 was preswollen in 0.1M Tris-HCl pH 7.0 supplemented with 1.0M NaCl and poured into a 50 ml column. The column was then equilibrated in 0.1M Tris pH 7.0. The pooled cathepsin L-like protease was reapplied twice at 4° C. to ensure maximum binding of non-cathepsin L proteins present in the E/S products. The flowrate of the column was approximately 1 ml/min. The run through fraction i.e. the fraction containing proteins not adsorbed to the QAE Sephadex (approximately 50 ml) was collected and concentrated to a volume of 10 ml by ultrafiltration with a membrane having a 3000 mw cut off, dialysed against ultra-pure water and freeze dried.

The final specific activity of the purified cathepsin-L1 proteinease was $11.67 \times 10^3$ units/mg protein (where one unit releases 1 $\mu$mol of AMC/min).

Figure 1B:
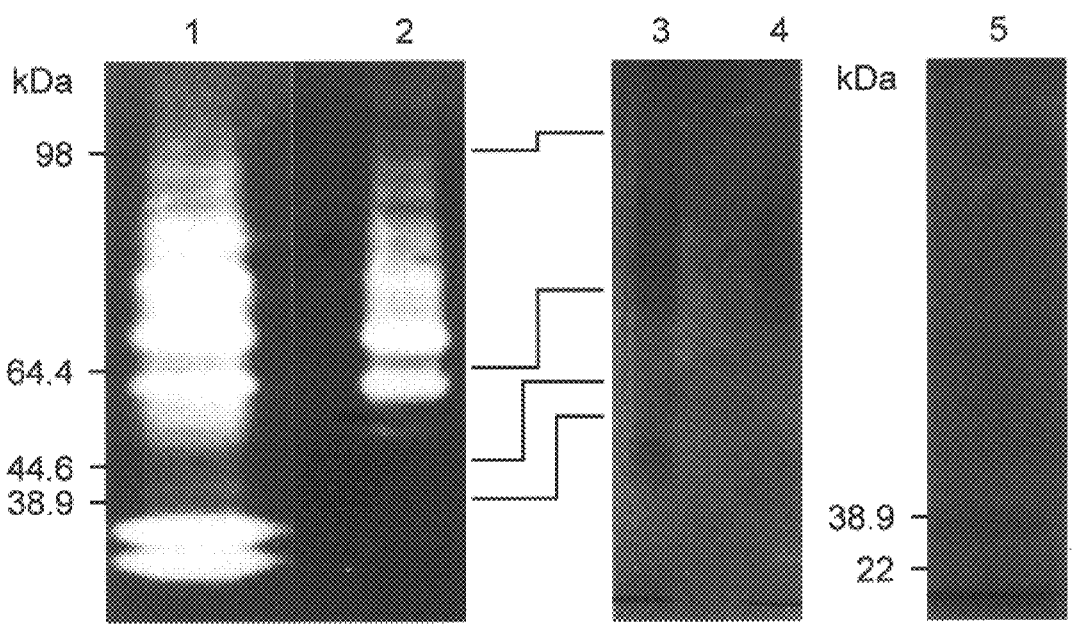

Samples from the purification were taken and loaded onto GS, SDS-non-reducing and SDS-reducing polyacrylamide gels (10% acrylamide, 0.1% SDS) in order to evaluate the proteinase activity, and to establish the purity of the cathepsin-L1. The result is shown in FIG. 1B in which lanes 1 and 3 are total E/S products on GS and SDS non-reducing gels, lanes 2 and 4 are the purified Cathepsin L1 on GS and SDS non-reducing gels while lane 5 is purified Cathepsin L1 on an SDS gel under reducing conditions. GS-PAGE analysis showed that the purified cathepsin-L1 enzyme consisted of multiple bands of proteinase activity in the molecular weight range 60 KDa and higher (FIG. 1B, lane 2, cf. Dalton & Heffernan referred to above), these bands correspond to bands of similar molecular weight on an SDS non-reducing gel while on the SDS-reducing gel these multiple bands were resolved into one band of molecular weight 27 KDa (FIG. 1B, lane 5).

2) N-TERMINAL SEQUENCE DETERMINATION

To confirm the classification of this purified enzyme as a cathepsin L-like proteinase, a concentrated sample of pooled cathepsin-L1 from the gel filtration column was sequenced using an Applied Biosystems 477A protein sequencer. The resulting amino-acid sequence was aligned with previously determined sequences of known cathepsin-L molecules and the catheps in-B sequence of *Schistosoma mansoni* (Table 1 below). Identical residues to those in *F. hepatica* cathepsin-L1 are shown by the dots. In the first 19 residues of the N-terminal sequence the fluke cathepsin-L has 63% identity with cathepsin-L molecules from both bovine and chicken liver sources, 53, 59 and 53% homology with cathepsin-L molecules from rat, human and *Tryanosoma cruzi* respectively, and 26% homology with a cathepsin-B from *S. mansoni*

|  | -1 | 1 | 2 | 3 | 4 | 5 | 6 | 7 | 8 | 9 | 10 | 11 | 12 | 13 | 14 | 15 | 16 | 17 | 18 | 19 | |
|---|---|---|---|---|---|---|---|---|---|---|---|---|---|---|---|---|---|---|---|---|---|
| F. hepatica (C-L1) | A | V | P | D | K | I | D | P | R | E | S | G | - | - | Y | V | T | - | - | G | V | K | D | Q | (Seq. ID No: 1) |
| Bovine (C-L) |  | L | P | D | S | V | D | W | R | E | K | G | - | - | G | V | T | - | - | P | V | K | D | Q | (Seq. ID No: 2) |
| Chicken liver (C-L) | - | A | P | R | S | V | D | W | R | E | K | G | - | - | Y | V | T | - | - | P | V | K | D | Q | (Seq. ID No: 3) |
| Rat liver (C-L) | - | I | P | R | S | V | D | W | R | E | K | G | - | - | Y | V | T | - | - | P | V | K | D | Q | (Seq. ID No: 4) |
| Human liver (C-L) | - | A | P | R | S | V | D | W | R | E | K | G | - | - | Y | V | T | - | - | P | V | K | D | Q | (Seq. ID No: 5) |

-continued

|  | -1 | 1 | 2 | 3 | 4 | 5 | 6 | 7 | 8 | 9 | 10 | 11 |  | 12 | 13 | 14 |  | 15 | 16 | 17 | 18 | 19 |  |
|---|---|---|---|---|---|---|---|---|---|---|---|---|---|---|---|---|---|---|---|---|---|---|---|
| T. cruzi (c-p) | - | A | P | A | A | V | D | W | R | A | R | G | - - | A | V | T | - - | A | V | K | D | Q | (Seq. ID No: 6) |
| S. mansoni (C-B) | - | I | P | S | N | F | D | S | R | K | K | W | P G | C | K | S | I A | T | I | R | D | Q | (Seq. ID No: 7) |

3) CATHEPSIN-L1 ANTIBODY PRODUCTION

Polyclonal antiserum against cathepsin-L1 was raised in white rabbits by subcutaneous injection of 52 μg of purified enzyme in complete Freund's adjuvant. Initial immunization was followed by boosts of 52 μg of enzyme in incomplete adjuvant at 40 days, 90 days, 120 days and 150 days; 1 week later the animals were bled. The antibody titre was determined using ELISA. Microtitre plates were coated with 50 μl of adult E/S products and left uncovered at 37° C. overnight. IgG2a immunoglobulins were purified from the anti-serum using a protein-A column.

4) WESTERN BLOTTING EXPERIMENTS

Western blot immuno-analysis was used to determine the specificity and consequently the cross-reactivity of rabbit antibodies raised against the purified proteinase cathepsin L1 from F. hepatica. These were carried out using E/S products and purified cathepsin-L1. Proteins were separated by SDS-PAGE and electrophoretically transferred to nitro-cellulose paper using a semi-dry blotting system. One percent fetal calf serum (FCS), and 0.5% Tween-20 in PBS was used to block any non-specific binding sites. The nitrocellulose was incubated with anti-Cathepsin-L1, and the bound immunoglobulin was detected using alkaline phosphatase-conjugated anti-rabbit serum. Nitro blue tetrazolium and 5-bromo-5-chloro-3-indolyl phosphate prepared in dimethylformamide were used as substrate.

The purified immunoglobulins showed no reaction with other proteins present in the E/S products and all of their binding specificity was confined to the protein bands (MW 60 KDa and higher on SDS-PAGE under non-reducing conditions) in the E/S products responsible for the proteinase activity of the purified cathepsin-L1. A blot of SDS-PAGE run under reducing conditions, probed with the anti-cathepsin-L1 antiserum, showed specific binding with only one band of protein MW 27 KDa in both E/S and purified cathepsin-L1 which correlates to the single band of protein seen when an SDS reducing gel of the purified cathepsin-L1 is run.

5) INHIBITION OF ENZYME ACTIVITY

To determine whether the anti-cathepsin-L1 antibody raised in the rabbit inhibited the activity of the cathepsin-L1, the purified antibodies were used as follows. FIG. 2A shows a 10% gelatin substrate non-reducing polyacrylamide gel, loaded with cathepsin-L1 and increasing amounts of anti-cathepsin-L1 IgG. It is evident from this gel that with increasing concentrations of anti-cathepsin-L1 IgG, the proteinase activity of the enzyme decreases as shown by the decreasing intensity of the clear bands on the dark background (lanes 1–7), whereas similar concentrations of non-immune rabbit IgG had no effect on the proteinase activity of cathepsin-L1 (lane 8 cathepsin L alone, lane 9 cathepsin L with non-immune rabbit IgG).

One of the most striking properties of the Cathepsin-L1 from F. hepatica is its ability to cleave antibody at the hinge region. Purified cathepsin-L1 was mixed with anti-cathepsin-L1 IgG or control IgG, incubated at 37° C., samples taken at various time intervals and the antibody molecules in the reaction mixture analysed by SDS-PAGE. Densitometric scans of these gels demonstrate that the binding of the anti-cathepsin-L1 to the enzyme prevents it from gaining access to the cleavage site in the antibody heavy chain; hence, the peaks representing the fragments generated from digestion of the heavy chain (FIG. 2, panel B, (ii)), are much reduced compared to those observed when cathepsin-L1 is incubated with control IgG (FIG. 2, panel B(i)).

6) CHARACTERISATION OF IGG CLEAVING ENZYME IN ADULT FLUKE E/S PRODUCTS

A mouse monoclonal antibody IgG2a obtained by known methods was used as a model substrate. The antibody was incubated with a sample of adult F. hepatica E/S products, or with the thiol proteinase papain. SDS-PAGE analysis revealed that proteinases in the E/S products cleave the mouse IgG2a heavy chain into two fragments. These fragments were similar in molecular size to the fragments produced by papain. Therefore, adult flukes secrete an enzyme capable of cleaving IgG2a close to the papain cleaving site, that is, within the hinge region of the antibody heavy chain. The fluke enzyme is not specific for IgG2a antibodies but also cleaved mouse IgG2b and IgG1a purified by protein-A affinity chromatography from whole mouse and rabbit serum.

Mature fluke E/S products were also analysed by HPLC. E/S products were concentrated ten-fold by freeze-drying and dialysed overnight against 0.1M potassium phosphate, pH 7.0. The dialysate was then filtered through a 0.45 μM membrane filter (Gelman Sciences, Michigan, USA) and 100 μg samples subjected to molecular sieve HPLC on a TSK3000SW column (Waters, Milford, USA). The mobile phase was 0.1M potassium phosphate, pH 7.0, the flow rate was 0.3 ml/min and the eluted proteins were monitored by absorbance at 280 nm using a sensitivity range of 0.05. The molecular sizes of proteins were determined by calibrating the column with the following proteins; IgG2a (150 kDa), bovine serum albumin (67 kDa), horse radish peroxidase (45 kDa) and lysozyme (14.3 kDa).

Figure 3A:
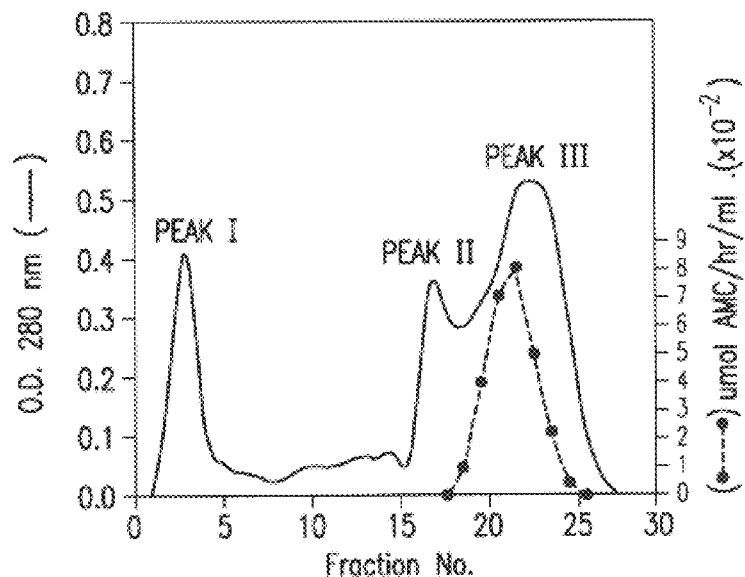
Figure 3B:
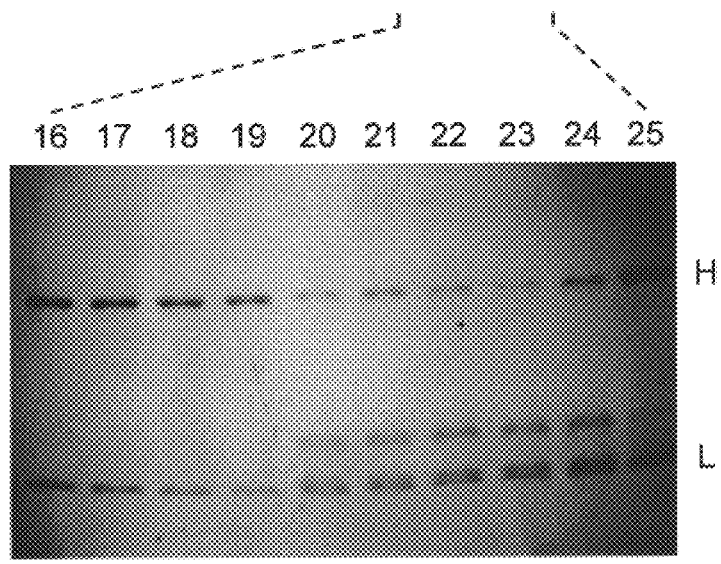

Analysis by GS-PAGE of the proteins eluted from HPLC yielded three major protein peaks of >150 kDA (Peak I), 45 kDa (Peak II) and 15 kDa (Peak III), see FIG. 3a. A sample of each fraction was incubated with the IgG2a monoclonal antibody and the products of the reaction subjected to SDS-PAGE. The IgG2a cleaving enzyme was associated with the third, 15 kDa, peak, see FIG. 3b.

Figure 3C:
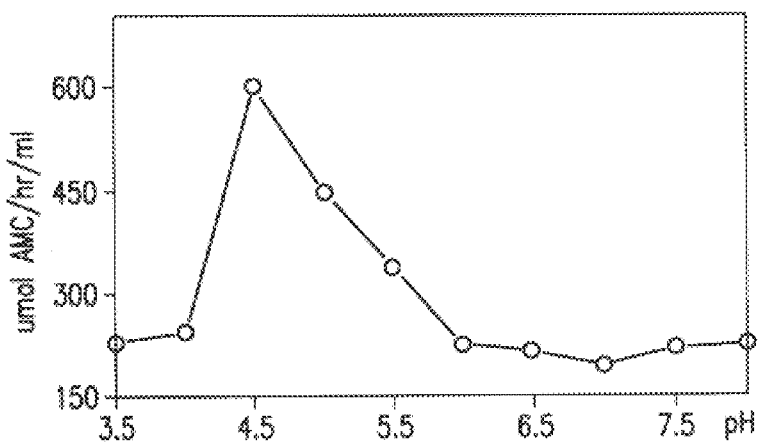

Each fraction was also tested for-Cathepsin L-like activity using the synthetic peptide substrate Z-phe-arg-AMC. Cathepsin L-like activity was associated with the 15 kDa peak. The optimum pH for Cathepsin L-like activity was determined for the 15 kDa protease using Z-phe-arg-AMC, see FIG. 3C.

GS-PAGE analysis was then carried out on pooled fractions from each peak. The proteolytic bands detected in the total adult fluke E/S products using GS-PAGE were present in either the 45 kDa or 15 kDa peak, no proteinases were associated with the >150 kDa peak GS-PAGE analysis of the 45 kDa Peak II showed that it contained several proteinases ranging from 46 to 27.5 kDa; these proteinases correlated exactly with the Group 2 proteinases described by Dalton and Heffernan [Mol. Biochem Parasitol. 35 (1989)] as having optimal activity between pH 4.5–8.0. The 15 kDa peak consisted of several proteinases; these enzymes showed surprisingly high apparent molecular sizes ranging between 60–90 kDa. These proteinases correlated with the Group 1 thiol proteinases described by Dalton and Heffernan [ibid] that have a pH optimum for activity at pH 4.5.

Clearly therefore the Cathepsin-L1 molecule demonstrated as having a 27 kDa molecular weight by SDS-PAGE under reducing conditions shows various aberrant molecular weights depending on the technique used, thus on HPLC an abnormally low molecular weight is observed while on GS-PAGE autolysis and aggregation appear to give a series of higher molecular weight bands.

7) CATHEPSIN L-LIKE ACTIVITY IN E/S PRODUCTS OF VARIOUS STAGES OF F. hepatica F. hepatica metacercariae (Pfizer strain) encysted on cellophane were removed with a Pasteur pipette into 2% sodium hypochlorite, vortexed and incubated for 30 minutes at 37° C. This procedure removes the outer cyst of the metacercariae. The metacercariae, now only with the inner transparent cyst, were placed into microtitre wells with an automatic pipette using a stereomicroscope and washed in distilled water. They were then incubated in a medium prepared by mixing equal volumes of 0.05M HCl with a solution containing 1% sodium bicarbonate, 0.8% NaCl and 0.2% sodium taurocholate. After 3 hours at 37° C. 70–80% of the flukes were excysted and actively moving. The excysted juveniles were separated from the inner cysts using a 20 $\mu$l automatic pipette under a stereomicroscope.

Mature flukes were removed from the bile ducts of bovine livers obtained at an abbatoir. Immature parasites were obtained from the liver of male Wistar rats three and five weeks after infection with 20 metacercariae.

Newly excysted juvenile (NEJ), 3 week-old, 5 week-old and mature F. hepatica were maintained in vitro over a period of 3 days. The culture medium, removed daily, was then assayed for Cathepsin L-like activity using the fluorogenic substrate Z-phe-arg-AMC. Cathepsin L-like activity was present in the E/S products from all stages examined. Whilst the Cathepsin L-like activity increased on a daily basis in the NEJ E/S products, indicating an increase in its secretion with time, the activity of this proteinase in the EIS of all other stages decreased over the same time period. The proteinase activity in the E/S of each liver fluke stage was compared using three arginine-containing fluorogenic peptide substrates. These substrates were chosen on the basis of their affinity for lysosomal cathepsin enzymes; cathepsin L (Z-phe-arg-AMC), cathepsin B (Z-arg-arg-AMC) and cathepsin H (Z-arg-AMC). Significant activity was only detected using the Z-phe-arg-AMC substrate and similar results were obtained for all liver fluke stages examined (Table 2 below).

TABLE 2

Specific activity against fluorogenic substrates by E/S products from various liver fluke developmental stages*

| Substrate | NEJ | 3 weeks | 5 weeks | Adults |
|---|---|---|---|---|
| Z-Phe-Arg-AMC | 25 | 29 | 90 | 1254 |
| Z-Arg-Arg-AMC | 0 | 0 | 2 | 21 |
| Z-Arg-AMC | 1 | 3 | 5 | 63 |

*values represent means of duplicate results in $\mu$mol AMC/min/Mg

8) ANTIBODY-CLEAVING ACTIVITY IN E/S PRODUCTS

As IgG is involved in antibody-dependent cellular cytotoxicity against helminth parasites and since adult fluke Cathepsin-L1 cleaves mouse IgG2a [see above], the E/S products from NEJ, 3 week-old, 5 week-old and adult flukes were tested for antibody cleaving activity. E/S products from all F. hepatica stages examined were capable of cleaving the purified IgG at the hinge region of the heavy chain and thereby releasing the Fc portion from the antibody binding regions. The Cathepsin-L inhibitor, Z-phe-ala-CHN$_2$, at a final concentration of 50 $\mu$M completely inhibited the IgG cleaving activity of the E/S products-from adult and NEJ flukes. DMSO, at a final concentration of 1%, did not inhibit the IgG cleaving activity.

9) EFFECTS OF E/S PRODUCTS AND CATHEPSIN L1 PROTEINASE ON EOSINOPHIL ADHERENCE

The possible role of the F. hepatica Cathepsin L1 in preventing antibody-mediated attachment of eosinophils to NEJ was examined using an in vitro assay.

Twenty newly excysted juvenile F. hepatica were dispensed into 100 $\mu$l of rat eosinophil-rich suspension in microtitre wells. According to the experiment either 100 $\mu$l aliquots of immune serum or control serum were added with or without E/S products or purified Cathepsin L1. The cysteine proteinase inhibitor leupeptin was added in some experiments at a final concentration of 5 $\mu$g/ml. All dilutions were made in Roswell Park Memorial Institute 1640 with 4% heat inactivated fetal calf serum. At the end of the experiment juvenile flukes were carefully transferred to a microscope slide and examined microscopically at 40× and 100× magnifications. Individual flukes were examined and the number of bound eosinophils counted. Those NEJ with more than 20 cells attached were considered positive.

Figure 4:
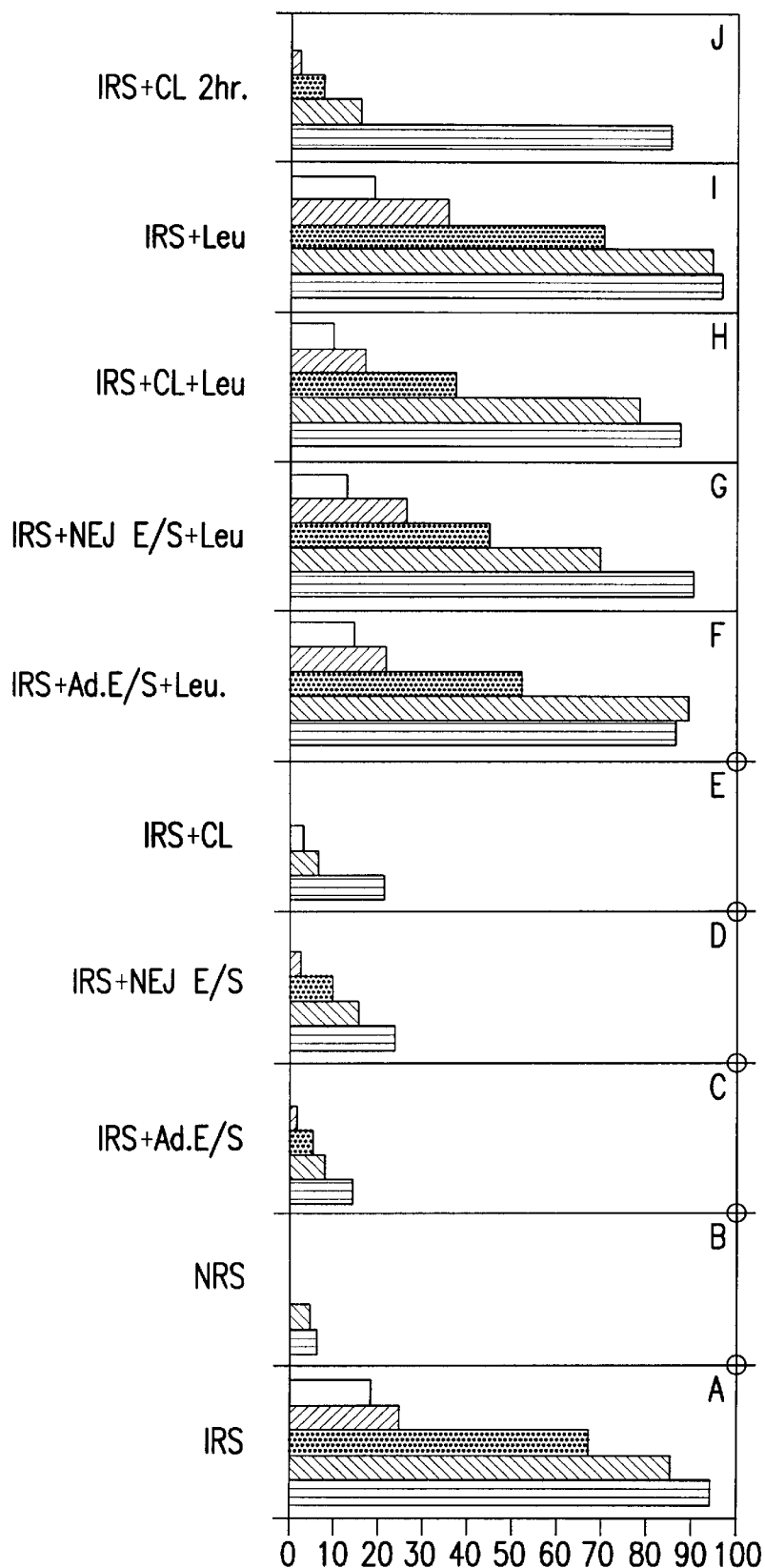

When rat eosinophil-rich cell populations were added to NEJ in the presence of immune rat serum (IRS obtained from female Wistar rats orally infected with 30 F. hepatica metacercariae; blood was taken after 5 weeks of infection; the sera obtained were pooled, aliquoted and stored at −20° C. until required; control serum was collected from uninfected rats), cell adherence was consistently high (>90% positive NEJ after 2 hours, FIG. 4, panel A; the scale along the base of the Figure represents percentage of positive NEJ as defined above; the 5 bars represent counts at 2 hour intervals). This cellular adherence was not observed in the presence of normal serum (FIG. 4, panel B) and hence it must be presumed that it is mediated by anti-NEJ antibodies. The maximum cell attachment was registered after 2 hours of incubation. Addition of NEJ or mature fluke E/S products, together with immune serum, resulted in a >70% reduction in the number of positive NEJ as compared to immune serum alone (FIG. 4, panels C and D). Similarly, purified Cathepsin L1 prevented the attachment of eosinophils (FIG. 4, panel E). When the cysteine proteinase inhibitor, leupeptin, was added in the presence of immune serum and either NEJ or mature fluke E/S products or purified Cathepsin L1, eosinophil attachment was similar to that obtained using immune serum alone (FIG. 4, panels A, F, G and H); hence leupeptin inhibits the effect of the E/S products and Cathepsin L1. Leupeptin added to NEJ in culture did not affect their viability (data not shown) although in the presence of immune serum it slightly reduces the rate at which eosinophils are lost from the NEJ surface (FIG. 4, panel I). When purified Cathepsin L1 was added to the assay 2 hours after the addition of immune serum, thereby allowing eosinophils initially to attach, these attached eosinophils were quickly detached from the NEJ surface (FIG. 4, panel J, compare panels A and E).

10) CATTLE TRIALS

Eighteen cattle were housed indoors. The cattle were allocated into 5 groups, A, B, C, D and E, each of three or four cattle and acclimatised for a period of 7 days. Primary immunisation occurred on day 0. Animals in group A were negative controls and received 150 µg of horse spleen ferritin, groups B, C, D and E received 10, 50, 200 and 500 µg of Cathepsin L1 respectively prepared as described under (1) above, all by injection. Primary immunisations were adjuvanted in Freund's complete adjuvant (FCA). Twenty-eight days later all animals received a secondary immunisation and also a tertiary vaccination at day 56. These vaccinations were adjuvanted in Freund's incomplete adjuvant (FIA). Antibody titres were monitored throughout this period. On day 76 all animals received 25 ml levamisole after nematode eggs were found in faecal samples from some of them.

On day 84 all groups of cattle received an exogenous challenge of ca 500 liver fluke metacercariae administered by gelatin capsule from a dosing gun (*F. hepatica* was of UK origin). The progress of the infection was monitored via levels of enzymes in the blood and faecal egg counts.

Summary of animal groups:

| Group ID | Number of Animals | Vaccination |
|---|---|---|
| A | 4 | 150 µg horse spleen ferritin |
| B | 4 | 10 µg Cathepsin L1 |
| C | 4 | 50 µg Cathepsin L1 |
| D | 3 | 200 µg Cathepsin L1 |
| E | 3 | 500 µg Cathepsin L1 |

All animals responded to immunisation as determined by ELISA—following challenge all animals showed increased serum levels of glutamic dehydrogenase and glutamyl gamma transferase, indicative respectively of liver parenchyma and bile duct damage caused by the liver flukes. Only animals in the control group showed eggs in faeces.

11) CATHEPSIN-L2 PURIFICATION

Flukes were washed, cultured and the culture medium centrifuged as described above for Cathepsin L1. Five hundred ml of the E/S products were thawed, concentrated to a volume of 10 ml on an Amicon 8400 concentrator (Amicon, Wis., USA) using an Amicon YM3 membrane (3,000 Da m.w. cut-off), and applied to a gel filtration column containing Sephacryl S200HR resin (1.9 cm×42 cm, Pharmacia, Uppsala, Sweden) equilibrated in 0.1M tris-HCl pH 7 at 4° C. The column was eluted with 0.1M Tris-HCl pH 7 and 70×5 ml fractions were collected. The fractions containing cathepsin L2 activity, assayed, using the fluorogenic substrate Tos-Gly-Pro-Arg-AMC in 0.1M glycine at pH 7, on a Perkin-Elmer Fluorescence spectrophotometer with an excitation wavelength of 370 nm and an emission filter setting of 440 nm, were pooled.

The Sephacryl S200 fraction was applied to a 50 ml QAE Sephadex column (2.5 cm×10.0 cm, Pharmacia, Uppsala, Sweden) equilibrated in 0.1M tris-HCl pH 7. The QAE Sephadex column was washed with 300 ml of 0.1M Tris-HCl pH 7 and 150 ml of 75 mM NaCl in 0.1M Tris-HCl pH7 and was subsequently eluted with 250 ml of 0.4M NaCl in 0.1M Tris-HCl pH 7. Five ml fractions from each washing and elution step (180 fractions in total) were collected. The fractions found to contain Tos-Gly-Pro-Arg-AMC cleaving activity were pooled (QAE400 fraction). The QAE400 fraction was concentrated to 20 ml on a Amicon 8400 concentrator using a YM3 membrane and then diluted with distilled water to a volume of 100 ml. The diluted QAE400 fraction was then concentrated to a final volume of 10 ml containing a NaCl concentration calculated to be approximately 80 mM. The concentrated QAE400 fraction was stored as 10×1 ml aliquots at −80° C.

The homogeneity of the purified cathepsin L2 was determined using denaturing SDS-PAGE gels containing 12% polyacrylamide. The purified cathepsin L2 migrates as a single band of 29.5 kDa on a reducing SDS-PAGE gel (FIG. 5C, lane 1 molecular weight markers, lane 2 adult fluke E/S products, lane 3 purified Cathepsin L2).

Zymography was performed using 12% PAGE gels according to the method of Dalton and Heffernan, Mol. Biochem. Parasitol. 35 (1989) p. 161–166, both in the presence and absence of SDS. Analysis in the presence of SDS shows that the enzyme migrates as 4 bands which are also observed in the total adult fluke E/S products (FIG. 5A, lane 1 adult fluke E/S products, lane 2 purified cathepsin L2). However, zymography in the absence of SDS shows that the purified cathepsin L2 migrates as a single proteolytic band (FIG. 5B, lanes as in FIG. 5A).

12) AMINO-TERMINAL SEQUENCE ANALYSIS

A 5.4 ml aliquot of E/S products (5 mg protein approx.) was concentrated to 200 µl by freeze-drying. Forty µl of concentrated sample was applied to a non-denaturing 12% SDS-PAGE gel and electrophoresed as described above. After electrophoresis the gel was incubated for 30 minutes in transfer buffer (25 mM Tris, 190 mM glycine and 10% (v/v) methanol). A strip of PVDF (Problott) membrane (10 cm×4.5 cm) was immersed in methanol for 10 sec followed by equilibration in transfer buffer for 5 minutes. Separated proteins were transfered to the PVDF membrane using a semi-dry electroblotting apparatus (Atto corp., Tokyo, Japan) according to the manufacturers instructions. The membrane was stained and destained and air-dried and the protein bands of interest were cut out and sequenced on an Applied Biosystems 477A protein sequencer at the University of Cambridge.

The N-terminal sequence is given below in Table 3 aligned with N-terminal sequences determined for *F. hepatica* cathepsin L1, cathepsin L from chicken, rat and human livers, cathepsin S from bovine spleen, a Cathepsin L-like protease from *T.cruzi* (cruzipain) and cathepsin B from *S. mansoni*. It can be seen cathepsin L1 is 93% homologous to cathepsin L2 (one amino acid, arginine in position 7 in cathepsin L2 is substituted for a proline in position 7 in cathepsin L1). Cathepsin L2 is only 47% homologous to chicken liver cathepsin L, rat liver cathepsin L and human liver cathepsin L, 47% homologous to bovine spleen cathepsin S, 40% homologous to the *T. cruzi* cathepsin L-like protease (cruzipain) and 20% homologous to *S. mansoni* cathepsin B.

By contrast with the two chain structure known to exist for mammalian Cathepsin L, the finding of a single N-terminal amino acid sequence for both Cathepsin L1 and L2 implies the presence of only a single chain. It is however possible that a second N-terminally blocked chain is present.

|  | -1 | 1 | 2 | 3 | 4 | 5 | 6 | 7 | 8 | 9 | 10 | 11 | 12 | 13 | 14 |  |
|---|---|---|---|---|---|---|---|---|---|---|---|---|---|---|---|---|
| *F. hepatica* (cathepsin L2) |  | A | V | P | D | K | I | D | R | R | E | S | G | - | - | Y | V |  | (Seq. ID No: 8) |
| *F. hepatica* (cathepsin L1) |  | A | V | P | D | K | I | D | P | R | E | S | G | - | - | Y | V | T | (Seq. ID No: 9) |
| Chicken liver (cathepsin L) | - | A | P | R | S | V | D | W | R | E | K | G | - | - | Y | V | T | (Seq. ID No: 11) |
| Rat liver (cathepsin L) | - | I | P | R | S | V | D | W | R | E | K | G | - | - | Y | V | T | (Seq. ID No: 11) |
| Human liver (cathepsin L) | - | A | P | R | S | V | D | W | R | E | K | G | - | - | Y | V | T | (Seq. ID No: 12) |
| Bovine spleen (cathepsin S) |  | L | P | D | S | M | D | W | R | E | K | G | - | - | C | V | T | (Seq. ID No: 13) |
| *T. cruzi* (c-p) | - | A | P | A | A | V | D | W | R | A | R | G | - | - | A | V | T | (Seq. ID No: 14) |
| *S. mansoni* (C-B) | - | I | P | S | N | F | D | S | R | K | K | W | P | G | C | K | S | (Seq. ID No: 15) |

13) KINETIC STUDIES

The kinetic constants of *F. hepatica* cathepsins L1 and L2 enzymes were determined for 11 different substrates: Z-Phe-Arg-AMC, Bz-Phe-Val-Arg-AMC, Suc-Leu-Leu-Val-Tyr-AMC, H-Leu-Val-Tyr-AMC, Tos-Gly-Pro-Lys-AMC, Tos-Gly-Pro-Arg-AMC, Boc-Val-Pro-Arg-AMC, Z-Arg-Arg-AMC, Z-Arg-AMC, Suc-Ala-Phe-Lys-AMC and Boc-Val-Leu-Lys-AMC. One mg of fluorogenic substrate was dissolved in 100 $\mu$l of dimethyl formamide. This stock solution was diluted in 0.1M glycine pH 7.0 to achieve the desired concentration of substrate. Each substrate concentration was in triplicate and the final assay volume was 1.0 ml. Included in the 1 ml aliquot was 20 $\mu$l of enzyme and 50 $\mu$l of 10 mM dithiothreitol. The samples were incubated at 37° C. for 30 min before stopping the reaction with the addition of 200 $\mu$l of 1.7 M acetic acid. The samples were assayed for released 7-amino-methyl-coumarin as above. The kinetic constants $V_{max}$ and $K_m$ were obtained by non-linear regression according to the method of Barrett et al (Biochem J. 201, p.189–198) except that 20 $\mu$l of cathepsin L2 was incubated with 20 $\mu$l of 1.0 $\mu$M–0.1 $\mu$M E-64 in a final volume of 80 $\mu$l 0.1M glycine pH 7.0 for 30 mins at 37° C. Twenty $\mu$l of 1/10 cathepsin L1 was incubated with 20 $\mu$l of 5 $\mu$M–0.5 $\mu$M E-64 in a final volume of 80 $\mu$l 0.1M glycine pH 7.0 for 30 min. at 37° C. All of the incubated sample was assayed for the fluorogenic substrate Z-Phe-Arg-AMC as above.

The kinetic constant results are shown in Table 4. The data show that both enzymes favour the substrate Boc-Val-Leu-Lys-AMC with cathepsin L2 having 2.5 times the affinity ($k_{cat}/K_m$) for Boc-Val-Leu-Lys-AMC of cathepsin L1. The second best substrate was Z-Phe-Arg-AMC with cathepsin L2 having 2 times higher affinity for this substrate than cathepsin L1. Cathepsin L2 cleaves the fluorogenic substrates H-Leu-Val-Tyr-AMC, Bz-Phe-Val-Arg-AMC, Tos-Gly-Pro-Lys-AMC, Tos-Gly-Pro-Arg-AMC and Boc-Val-Pro-Arg-AMC with similar affinities ($k_{cat}/K_m$=38–113 $10^{-3} M^{-1}.S^{-1}$). Cathepsin L1 does not cleave these substrates to any significant degree ($k_{cat}/K_m$=0.26–3.89 $10^{-3}$ $M^{-1}.S^{-1}$).

TABLE 4

Enzyme kinetic studies of *F. hepatica* cathepsins L1 and L2.

| Enzyme | Sustrate | $K_M$ ($\mu$M) | $K_{cat}$ ($s^{-1}$) | $K_{cat}/K_m$ ($10^3 s^{-1} \cdot M^{-1}$) |
|---|---|---|---|---|
| Cathepsin L2 | z-Arg-AMC | 14.08 | 0.09 | 6.39 |
| | z-Arg-Arg-AMC | 9.07 | 0.02 | 2.21 |
| | z-Phe-Arg-AMC | 3.76 | 0.56 | 148.9 |
| | Bz-Phe-Val-Arg-AMC | 1.20 | 0.06 | 45.83 |
| | H-Leu-Val-Tyr-AMC | 3.75 | 0.21 | 55.47 |
| | Suc-Leu-Leu-Val-Tyr-AMC | 23.33 | 0.08 | 3.25 |
| | Boc-Val-Pro-Arg-AMC | 24.81 | 1.19 | 47.96 |
| | Tos-Gly-Pro-Arg-AMC | 17.06 | 1.93 | 113.3 |
| | Tos-Gly-Pro-Lys-AMC | 35.49 | 1.37 | 38.60 |
| | Suc-Ala-Phe-Lys-AMC | 41.15 | 0.14 | 3.40 |
| | Boc-Val-Leu-Lys-AMC | 7.34 | 3.75 | 510.9 |
| Cathepsin L1 | z-Arg-AMC | 20.36 | 0.04 | 2.16 |
| | z-Arg-Arg-AMC | 65.60 | 0.002 | 0.03 |
| | z-Phe-Arg-AMC | 14.68 | 1.08 | 73.57 |
| | Bz-Phe-Val-Arg-AMC | 9.25 | 0.03 | 3.03 |
| | H-Leu-Val-Tyr-AMC | 5.40 | 0.02 | 3.89 |
| | Suc-Leu-Leu-Val-Tyr-AMC | 38.48 | 0.01 | 0.34 |
| | Boc-Val-Pro-Arg-AMC | 43.60 | 0.02 | 0.46 |
| | Tos-Gly-Pro-Arg-AMC | 26.04 | 0.03 | 1.23 |
| | Tos-Gly-Pro-Lys-AMC | 106.9 | 0.03 | 0.26 |
| | Suc-Ala-Phe-Lys-AMC | 65.32 | 0.05 | 0.77 |
| | Boc-Val-Leu-Lys-AMC | 34.70 | 7.90 | 227.7 |

14) *F.hepatica* CATHEPSIN L DNA SEQUENCES, CATHEPSIN L GENES IN OTHER HELMINTH PARASITES DNA sequences were obtained by amplification of *F.hepatica* cDNA using conventional polymerase chain reaction (PCR) techniques. The sequences are shown in FIGS. 6–8 (Seq. ID No: 16–21) with the amino acids for which they code. Genomic DNA from other helminth parasites was probed with the *F.hepatica* sequence JDCLONEC shown in FIG. 6 using the Southern blotting technique and conditions of moderate stringency. Bands were observed in the heartworm (Dirofilaria immitis) and blowfly (Lucilia cuprina) channels indicating respectively strong and weak hybridisation.

FIG. 9 is an autoradiograph of one such experiment in which column "A" is λ Hind markers, columns B, C and D are genomic DNA from *F.hepatica, Lucilia cuprina* and *Dirofilaria immitis*; Columns E, F and G are bovine, ovine and canine genomic DNA; and finally Column H is λ Hind markers again.

What is claimed is:

1. A vaccine for use in combating a parasitic infestation of helminths in a mammal, comprising antigenic material, wherein the antigenic material comprises *Fasciola hepatica* Cathepsin L1 having a molecular weight of 27 kDa by sodium dodecyl sulphate polyacrylamide gel electrophoresis under reducing conditions and being at least 95% pure, or an antigenic fragment or epitope thereof, together with an adjuvant and, optionally, a carrier.

2. A vaccine as claimed in claim 1 wherein the antigenic material is Cathepsin L1 having a molecular weight of 27 kDa by sodium dodecyl sulphate polyacrylamide gel electrophoresis under reducing conditions and an N-terminal sequence AVPDKIDPRESG[SEQ ID NO:22].

3. A method of combating a parasitic infestation of helminths in a mammal comprising administering to said mammal a vaccine as claimed in claim 1 in an amount effective to combat said infestation.

4. A method as claimed in claim 3 wherein said effective amount is within the range 10–500 µg.

5. A vaccine as claimed in claim 1 further comprising one or more purified antigenic proteins, wherein said proteins be excretory/secretory proteins.

6. A method as claimed in claim 3, wherein said antigenic material is Cathepsin L1 having a molecular weight of 27 kDa by sodium dodecyl sulphate polyacrylamide gel electrophoresis under reducing conditions and an N-terminal sequence AVPDKIDPRBSG[SEQ ID NO:22].

* * * * *

SEQUENCE LISTING

<160> NUMBER OF SEQ ID NOS: 22

<210> SEQ ID NO 1
<211> LENGTH: 20
<212> TYPE: PRT
<213> ORGANISM: Fasciola Hepatica

<400> SEQUENCE: 1

Ala Val Pro Asp Lys Ile Asp Pro Arg Glu Ser Gly Tyr Val Thr Gly
1               5                   10                  15

Val Lys Asp Gln
            20

<210> SEQ ID NO 2
<211> LENGTH: 19
<212> TYPE: PRT
<213> ORGANISM: Bovine

<400> SEQUENCE: 2

Leu Pro Asp Ser Val Asp Trp Arg Glu Lys Gly Gly Val Thr Pro Val
1               5                   10                  15

Lys Asp Gln

<210> SEQ ID NO 3
<211> LENGTH: 19
<212> TYPE: PRT
<213> ORGANISM: Chicken

<400> SEQUENCE: 3

Ala Pro Arg Ser Val Asp Trp Arg Glu Lys Gly Tyr Val Thr Pro Val
1               5                   10                  15

Lys Asp Gln

<210> SEQ ID NO 4
<211> LENGTH: 19
<212> TYPE: PRT
<213> ORGANISM: Rat

<400> SEQUENCE: 4

Ile Pro Arg Ser Val Asp Trp Arg Glu Lys Gly Tyr Val Thr Pro Val
1               5                   10                  15

Lys Asp Gln

<210> SEQ ID NO 5
<211> LENGTH: 19
<212> TYPE: PRT
<213> ORGANISM: Human

<400> SEQUENCE: 5

Ala Pro Arg Ser Val Asp Trp Arg Glu Lys Gly Tyr Val Thr Pro Val
1               5                   10                  15

Lys Asp Gln

<210> SEQ ID NO 6
<211> LENGTH: 19
<212> TYPE: PRT
<213> ORGANISM: Trypanosoma cruzi

<400> SEQUENCE: 6

Ala Pro Ala Ala Val Asp Trp Arg Ala Arg Gly Ala Val Thr Ala Val
1               5                   10                  15

Lys Asp Gln

<210> SEQ ID NO 7
<211> LENGTH: 23
<212> TYPE: PRT
<213> ORGANISM: S. mansoni

<400> SEQUENCE: 7

Ile Pro Ser Asn Phe Asp Ser Arg Lys Lys Trp Pro Gly Cys Lys Ser
1               5                   10                  15

Ile Ala Thr Ile Arg Asp Gln
            20

<210> SEQ ID NO 8
<211> LENGTH: 14
<212> TYPE: PRT
<213> ORGANISM: Fasciola Hepatica

<400> SEQUENCE: 8

Ala Val Pro Asp Lys Ile Asp Arg Arg Glu Ser Gly Tyr Val
1               5                   10

<210> SEQ ID NO 9

```
<211> LENGTH: 15
<212> TYPE: PRT
<213> ORGANISM: Fasciola Hepatica

<400> SEQUENCE: 9

Ala Val Pro Asp Lys Ile Asp Pro Arg Glu Ser Gly Tyr Val Thr
1               5                   10                  15

<210> SEQ ID NO 10
<211> LENGTH: 14
<212> TYPE: PRT
<213> ORGANISM: Chicken

<400> SEQUENCE: 10

Ala Pro Arg Ser Val Asp Trp Arg Glu Lys Gly Tyr Val Thr
1               5                   10

<210> SEQ ID NO 11
<211> LENGTH: 14
<212> TYPE: PRT
<213> ORGANISM: Rat

<400> SEQUENCE: 11

Ile Pro Arg Ser Val Asp Trp Arg Glu Lys Gly Tyr Val Thr
1               5                   10

<210> SEQ ID NO 12
<211> LENGTH: 14
<212> TYPE: PRT
<213> ORGANISM: Human

<400> SEQUENCE: 12

Ala Pro Arg Ser Val Asp Trp Arg Glu Lys Gly Tyr Val Thr
1               5                   10

<210> SEQ ID NO 13
<211> LENGTH: 14
<212> TYPE: PRT
<213> ORGANISM: Bovine

<400> SEQUENCE: 13

Leu Pro Asp Ser Met Asp Trp Arg Glu Lys Gly Cys Val Thr
1               5                   10

<210> SEQ ID NO 14
<211> LENGTH: 14
<212> TYPE: PRT
<213> ORGANISM: Trypanosoma cruzi

<400> SEQUENCE: 14

Ala Pro Ala Ala Val Asp Trp Arg Ala Arg Gly Ala Val Thr
1               5                   10

<210> SEQ ID NO 15
<211> LENGTH: 16
<212> TYPE: PRT
<213> ORGANISM: S. mansoni

<400> SEQUENCE: 15

Ile Pro Ser Asn Phe Asp Ser Arg Lys Lys Trp Pro Gly Cys Lys Ser
1               5                   10                  15

<210> SEQ ID NO 16
<211> LENGTH: 476
<212> TYPE: DNA
```

```
<213> ORGANISM: Fasciola Hepatica
<220> FEATURE:
<221> NAME/KEY: misc_feature
<222> LOCATION: (14)..(474)
<223> OTHER INFORMATION: n = unknown
<220> FEATURE:
<221> NAME/KEY: CDS
<222> LOCATION: (2)..(472)
<223> OTHER INFORMATION:

<400> SEQUENCE: 16
```

```
t cag gga aac tgt ngn ncc tgt tgg gca ttc tca aca acc ggt act atg      49
  Gln Gly Asn Cys Xaa Xaa Cys Trp Ala Phe Ser Thr Thr Gly Thr Met
   1               5                  10                  15 gag gga caa tat atg aaa aac gaa aaa act agt att tca ttc tct gag        97
Glu Gly Gln Tyr Met Lys Asn Glu Lys Thr Ser Ile Ser Phe Ser Glu
                 20                  25                  30 caa caa ctg gtc gat tgt agc ggt cct tgg gga aat aat ggt tgc agt       145
Gln Gln Leu Val Asp Cys Ser Gly Pro Trp Gly Asn Asn Gly Cys Ser
             35                  40                  45 ggt gga ttg atg gaa aat gct tac caa tat ttg aaa caa ttt gga ttg       193
Gly Gly Leu Met Glu Asn Ala Tyr Gln Tyr Leu Lys Gln Phe Gly Leu
         50                  55                  60 gaa acc gaa tcc tct tat ccg tac acg gct gtg gaa ggt cag tgt cga       241
Glu Thr Glu Ser Ser Tyr Pro Tyr Thr Ala Val Glu Gly Gln Cys Arg
65                  70                  75                  80 tac aat agg cag ttg gga gtt gcc aaa gtg acc ggc tac tat act gtg       289
Tyr Asn Arg Gln Leu Gly Val Ala Lys Val Thr Gly Tyr Tyr Thr Val
                 85                  90                  95 cat tct ggc agt gag gta gaa ttg aaa aat cta gtc ggt tcc gaa gga       337
His Ser Gly Ser Glu Val Glu Leu Lys Asn Leu Val Gly Ser Glu Gly
            100                 105                 110 cct gcc gcg atc gct gtg gat gtg gaa tct gac ttc atg atg tac agg       385
Pro Ala Ala Ile Ala Val Asp Val Glu Ser Asp Phe Met Met Tyr Arg
        115                 120                 125 agt ggt att tat cag agc caa act tgt tta ccg ttc gct ctg aat cat       433
Ser Gly Ile Tyr Gln Ser Gln Thr Cys Leu Pro Phe Ala Leu Asn His
    130                 135                 140 gca gtc ttg tct gtc ggt tat gga aca cag gat ggt act gntt             476
Ala Val Leu Ser Val Gly Tyr Gly Thr Gln Asp Gly Thr
145                 150                 155
```

```
<210> SEQ ID NO 17
<211> LENGTH: 157
<212> TYPE: PRT
<213> ORGANISM: Fasciola Hepatica
<220> FEATURE:
<221> NAME/KEY: misc_feature
<222> LOCATION: (5)..(6)
<223> OTHER INFORMATION: Xaa = unknown

<400> SEQUENCE: 17
```

```
Gln Gly Asn Cys Xaa Xaa Cys Trp Ala Phe Ser Thr Thr Gly Thr Met
 1               5                  10                  15

Glu Gly Gln Tyr Met Lys Asn Glu Lys Thr Ser Ile Ser Phe Ser Glu
                20                  25                  30

Gln Gln Leu Val Asp Cys Ser Gly Pro Trp Gly Asn Asn Gly Cys Ser
            35                  40                  45

Gly Gly Leu Met Glu Asn Ala Tyr Gln Tyr Leu Lys Gln Phe Gly Leu
        50                  55                  60

Glu Thr Glu Ser Ser Tyr Pro Tyr Thr Ala Val Glu Gly Gln Cys Arg
65                  70                  75                  80
```

```
Tyr Asn Arg Gln Leu Gly Val Ala Lys Val Thr Gly Tyr Tyr Thr Val
                85                  90                  95

His Ser Gly Ser Glu Val Glu Leu Lys Asn Leu Val Gly Ser Glu Gly
            100                 105                 110

Pro Ala Ala Ile Ala Val Asp Val Glu Ser Asp Phe Met Met Tyr Arg
        115                 120                 125

Ser Gly Ile Tyr Gln Ser Gln Thr Cys Leu Pro Phe Ala Leu Asn His
    130                 135                 140

Ala Val Leu Ser Val Gly Tyr Gly Thr Gln Asp Gly Thr
145                 150                 155

<210> SEQ ID NO 18
<211> LENGTH: 478
<212> TYPE: DNA
<213> ORGANISM: Fasciola Hepatica
<220> FEATURE:
<221> NAME/KEY: misc_feature
<222> LOCATION: (15)..(477)
<223> OTHER INFORMATION: n = unknown
<220> FEATURE:
<221> NAME/KEY: CDS
<222> LOCATION: (2)..(472)
<223> OTHER INFORMATION:

<400> SEQUENCE: 18 c cat caa gaa gcc cnn ggc tct tgt tgg gnt ttc tca aca aca ggt gct     49
  His Gln Glu Ala Xaa Gly Ser Cys Trp Xaa Phe Ser Thr Thr Gly Ala
  1               5                   10                  15 atg gaa gga cag tat atg aaa aac caa aga act agt att tca tnc tct       97
Met Glu Gly Gln Tyr Met Lys Asn Gln Arg Thr Ser Ile Ser Xaa Ser
                20                  25                  30 gag caa caa ctg gtc gat tgt agc cgt gat ttt ggc aat tat ggt tgt      145
Glu Gln Gln Leu Val Asp Cys Ser Arg Asp Phe Gly Asn Tyr Gly Cys
            35                  40                  45 aat ggt gga cta atg gaa aat gca tac gaa tat ttg aaa cga ttt gga      193
Asn Gly Gly Leu Met Glu Asn Ala Tyr Glu Tyr Leu Lys Arg Phe Gly
    50                  55                  60 ttg gaa acc gag tct tct tat cct tac agg gct gtg gaa gga caa tgt      241
Leu Glu Thr Glu Ser Ser Tyr Pro Tyr Arg Ala Val Glu Gly Gln Cys
65                  70                  75                  80 cga tac aac gag cag ttg gga gtt gcc aaa gtg act agc tac tat acg      289
Arg Tyr Asn Glu Gln Leu Gly Val Ala Lys Val Thr Ser Tyr Tyr Thr
                85                  90                  95 gta cat tct gga gat gag gta gaa ttg caa aat cta gtc ggt gcc gaa      337
Val His Ser Gly Asp Glu Val Glu Leu Gln Asn Leu Val Gly Ala Glu
            100                 105                 110 gga cct gct gcg gtc gct ttg gat gtg gag tca gac ttc atg atg tac      385
Gly Pro Ala Ala Val Ala Leu Asp Val Glu Ser Asp Phe Met Met Tyr
        115                 120                 125 agg agt ggt att tat cag agc caa act tgt tca ccg gat cgt ttg aac      433
Arg Ser Gly Ile Tyr Gln Ser Gln Thr Cys Ser Pro Asp Arg Leu Asn
    130                 135                 140 cat gga gtg ttg nct gtc gnt tat gga acn cag ggt ggt nctcnc           478
His Gly Val Leu Xaa Val Xaa Tyr Gly Xaa Gln Gly Gly
145                 150                 155

<210> SEQ ID NO 19
<211> LENGTH: 157
<212> TYPE: PRT
<213> ORGANISM: Fasciola Hepatica
<220> FEATURE:
<221> NAME/KEY: misc_feature
<222> LOCATION: (5)..(154)
```

<223> OTHER INFORMATION: Xaa = unknown

<400> SEQUENCE: 19

```
His Gln Glu Ala Xaa Gly Ser Cys Trp Xaa Phe Ser Thr Thr Gly Ala
1               5                   10                  15

Met Glu Gly Gln Tyr Met Lys Asn Gln Arg Thr Ser Ile Ser Xaa Ser
            20                  25                  30

Glu Gln Gln Leu Val Asp Cys Ser Arg Asp Phe Gly Asn Tyr Gly Cys
        35                  40                  45

Asn Gly Gly Leu Met Glu Asn Ala Tyr Glu Tyr Leu Lys Arg Phe Gly
    50                  55                  60

Leu Glu Thr Glu Ser Ser Tyr Pro Tyr Arg Ala Val Glu Gly Gln Cys
65                  70                  75                  80

Arg Tyr Asn Glu Gln Leu Gly Val Ala Lys Val Thr Ser Tyr Tyr Thr
                85                  90                  95

Val His Ser Gly Asp Glu Val Glu Leu Gln Asn Leu Val Gly Ala Glu
            100                 105                 110

Gly Pro Ala Ala Val Ala Leu Asp Val Glu Ser Asp Phe Met Met Tyr
        115                 120                 125

Arg Ser Gly Ile Tyr Gln Ser Gln Thr Cys Ser Pro Asp Arg Leu Asn
    130                 135                 140

His Gly Val Leu Xaa Val Xaa Tyr Gly Xaa Gln Gly Gly
145                 150                 155
```

<210> SEQ ID NO 20
<211> LENGTH: 473
<212> TYPE: DNA
<213> ORGANISM: Fasciola Hepatica
<220> FEATURE:
<221> NAME/KEY: misc_feature
<222> LOCATION: (1)..(470)
<223> OTHER INFORMATION: n = unknown
<220> FEATURE:
<221> NAME/KEY: CDS
<222> LOCATION: (2)..(466)
<223> OTHER INFORMATION:

<400> SEQUENCE: 20

```
n gcg aaa tgt ggt tcc tgt tgg gca ttc tca aca acc ggt act atg gag    49
  Ala Lys Cys Gly Ser Cys Trp Ala Phe Ser Thr Thr Gly Thr Met Glu
  1               5                   10                  15 gga caa tat atg aaa aac gaa aaa act agt ntt tca ncc tct gag caa      97
Gly Gln Tyr Met Lys Asn Glu Lys Thr Ser Xaa Ser Xaa Ser Glu Gln
            20                  25                  30 caa ctg gtc gat tgt agc ggt cct tgg gga aat aat ggt tgc agt ggt     145
Gln Leu Val Asp Cys Ser Gly Pro Trp Gly Asn Asn Gly Cys Ser Gly
        35                  40                  45 gga ttg atg gaa aat gct tac caa tat tta aaa caa ttt gga ttg gaa     193
Gly Leu Met Glu Asn Ala Tyr Gln Tyr Leu Lys Gln Phe Gly Leu Glu
    50                  55                  60 acc gaa tcc tct tat ccg tac acg gct gtg gaa ggt cag tgt cga tac     241
Thr Glu Ser Ser Tyr Pro Tyr Thr Ala Val Glu Gly Gln Cys Arg Tyr
65                  70                  75                  80 aat agg cag ttg gga gtt gcc aaa gtg act ggc tac tat act gtg cat     289
Asn Arg Gln Leu Gly Val Ala Lys Val Thr Gly Tyr Tyr Thr Val His
                85                  90                  95 tct ggc agt gag gca gga ttg aaa aat cta gtc ggt tcc gaa gga cct     337
Ser Gly Ser Glu Ala Gly Leu Lys Asn Leu Val Gly Ser Glu Gly Pro
            100                 105                 110 gcc gcg atc gct gtg gat gtg gaa tct gac ttc atg atg tac agg agt     385
```

```
Ala Ala Ile Ala Val Asp Val Glu Ser Asp Phe Met Met Tyr Arg Ser
            115                 120                 125 ggt att tat cag anc caa act tgt tta ccg ttc gct ttg aat cat gca         433
Gly Ile Tyr Gln Xaa Gln Thr Cys Leu Pro Phe Ala Leu Asn His Ala
            130                 135                 140 gtc ttg nct gtc gat tat gga aca cag gat ggt nacnccc                     473
Val Leu Xaa Val Asp Tyr Gly Thr Gln Asp Gly
145                 150                 155
```

<210> SEQ ID NO 21
<211> LENGTH: 155
<212> TYPE: PRT
<213> ORGANISM: Fasciola Hepatica
<220> FEATURE:
<221> NAME/KEY: misc_feature
<222> LOCATION: (27)..(147)
<223> OTHER INFORMATION: Xaa = unknown

<400> SEQUENCE: 21

```
Ala Lys Cys Gly Ser Cys Trp Ala Phe Ser Thr Thr Gly Thr Met Glu
1               5                   10                  15

Gly Gln Tyr Met Lys Asn Glu Lys Thr Ser Xaa Ser Xaa Ser Glu Gln
            20                  25                  30

Gln Leu Val Asp Cys Ser Gly Pro Trp Gly Asn Asn Gly Cys Ser Gly
            35                  40                  45

Gly Leu Met Glu Asn Ala Tyr Gln Tyr Leu Lys Gln Phe Gly Leu Glu
        50                  55                  60

Thr Glu Ser Ser Tyr Pro Tyr Thr Ala Val Glu Gly Gln Cys Arg Tyr
65                  70                  75                  80

Asn Arg Gln Leu Gly Val Ala Lys Val Thr Gly Tyr Tyr Thr Val His
                85                  90                  95

Ser Gly Ser Glu Ala Gly Leu Lys Asn Leu Val Gly Ser Glu Gly Pro
            100                 105                 110

Ala Ala Ile Ala Val Asp Val Glu Ser Asp Phe Met Met Tyr Arg Ser
            115                 120                 125

Gly Ile Tyr Gln Xaa Gln Thr Cys Leu Pro Phe Ala Leu Asn His Ala
            130                 135                 140

Val Leu Xaa Val Asp Tyr Gly Thr Gln Asp Gly
145                 150                 155
```

<210> SEQ ID NO 22
<211> LENGTH: 12
<212> TYPE: PRT
<213> ORGANISM: Fasciola Hepatica

<400> SEQUENCE: 22

```
Ala Val Pro Asp Lys Ile Asp Pro Arg Glu Ser Gly
1               5                   10
```